United States Patent [19]

Andre et al.

[11] Patent Number: 5,990,069
[45] Date of Patent: Nov. 23, 1999

[54] FUSARIUM ISOLATE AND LIPASES, CUTINASES AND ENZYME COMPOSITIONS DERIVED THEREFROM

[75] Inventors: Christophe Andre, Grez-Doiceau; Lucien Charmoille, Brussels, both of Belgium

[73] Assignee: Genencor International, Inc., Rochester, N.Y.

[21] Appl. No.: 08/849,824

[22] PCT Filed: Dec. 2, 1995

[86] PCT No.: PCT/EP95/04799

§ 371 Date: Oct. 27, 1997

§ 102(e) Date: Oct. 27, 1997

[87] PCT Pub. No.: WO96/18729

PCT Pub. Date: Jun. 20, 1996

[30] Foreign Application Priority Data

Dec. 13, 1994 [GB] United Kingdom .................... 9425109

[51] Int. Cl.$^6$ ................ D06L 16/00; C11D 7/42; C12N 9/20
[52] U.S. Cl. ............ 510/281; 510/320; 510/321; 435/198; 435/925
[58] Field of Search .................... 435/198, 925; 510/320, 321, 281

[56] References Cited

FOREIGN PATENT DOCUMENTS

| 130 064 | 1/1985 | European Pat. Off. . |
|---|---|---|
| 90/09446 | 8/1990 | WIPO . |
| 94/03578 | 2/1994 | WIPO . |
| 94/14951 | 7/1994 | WIPO . |
| 94/14963 | 7/1994 | WIPO . |
| 94/14964 | 7/1994 | WIPO . |

OTHER PUBLICATIONS

Chander & Klostermeyer, "Production of lipase by *Fusarium solani* under various growth conditions," Sciences Des Aliments, pp. 279–285 (1983).

Flurkey W.H. et al., "In vitro translation of cutinase mRNA:evidence for a precursor form of an extracellular fungal enzyme," Archives of Biochemistry and biophysics, vol. 212(1):154–161 (1981).

Koller W. et al., "Mechanism of Action of Cutinase Chemical Modification of the Catalytic Triad Characteristic for Serine Hydrolases," Biochemistry, vol. 21(13):3083–3090 (1982).

Martinez et al., "*Fusarium solani* cutinase is a lipolytic enzyme with a catalytic serine accessible to solvent," Nature, vol. 356 (6370):615–618 (1992).

Purdy & Kolattukudy, "Hydrolysis of plant cuticle by plant pathogens. Purification, amino acid composition and molecular weight of two isozymes of cutinase and a non-specific esterase from *Fusarium solani f. pisi*," Biochemistry, vol. 14, No. 13 (1975).

Purdy et al., "Depolymeriztion of a hydroxy fatty acid biopolymer, cutin, by an extracellular enzyme from *Fusarium solani f. pisi* Isolation and some properties of the enzyme," Arch. biochem. Biophys., vol. 159(1):61–69 (1973).

Soliday et al., "Isolation and characterization of a cutinase from *Fusarium roseum culmorum* and its immunological comparison with cutinases from *F. solani pisi*," Archives of Biochemistry and Biophysics, vol. 176:334–343 (1976).

Soliday et al., "Cloning and structure determination of cDNA for cutinase, an enzyme involved in fungal penetration of plants," Proc. Natl. Acad. Sci. USA, vol. 81:3939–3943 (1984).

Sreekantiah et al., "The production of certain extracellular hydrolytic enzymes by four species of plant pathogenic fungi," Indian Journal of Microbiology, vol. 12:71–78 (1972).

*Primary Examiner*—Herbert J. Lilling
*Attorney, Agent, or Firm*—Susan Faris

[57] ABSTRACT

The present invention concerns lipolytic enzymes naturally produced by a fungus of the species *Fusarium solanii*. The lipolytic enzymes include two lipases and a cutinase. The present invention concerns a biologically pure culture of *Fusarium solanii* producing these lipolytic enzymes and in particular a biologically pure culture of *Fusarium solanii* var. *minus* T.92.637/1. The present invention concerns also a detergent composition containing these lipolytic enzymes.

18 Claims, No Drawings

FUSARIUM ISOLATE AND LIPASES, CUTINASES AND ENZYME COMPOSITIONS DERIVED THEREFROM

The present invention relates to a novel, biologically pure culture of an isolate of the genus Fusarium, lipolytic enzymes, lipases, cutinases and enzyme compositions derived therefrom and, in particular, to a biologically pure culture of *Fusarium solanii* var. *minus* T.92.637/1, lipolytic enzymes, lipases, cutinases and enzyme compositions derived therefrom and the use of such enzymes in detergent compositions.

Lipolytic enzymes, including lipases and cutinases, are commonly employed in detergent cleaning compositions for the removal of fatty acid-based dirt and stains. As such, they have to be stable in presence of these detergents, and in particular in alkaline detergent solutions. Further, lipolytic enzymes are often used in combination with other enzymes, such as alkaline proteases, amylases, oxidases and/or other proteins, thereby requiring them to also be stable in presence of these enzymes.

Lipolytic enzymes naturally produced by various fungi are known.

European Patent Application 0 130 064 describes an enzymatic detergent additive including a lipase naturally produced by the fungal strain *Fusarium oxysporum*.

International Patent Application WO 90/09446 discloses an enzymatic detergent composition which includes a cutinase naturally produced by *Fusarium solanii* var. *pisi*.

To the best of our knowledge, we are not aware of any other lipolytic enzyme naturally produced by any other strains of Fusarium. Further, we are not aware of either any lipase or cutinase which has been naturally produced by any other species of Fusarium, including any isolate of the species *Fusarium solanii* var. *minus*.

It is a primary object of the present invention is to provide novel lipolytic enzymes naturally produced by a fungus of the species *Fusarium solanii*. By the term "lipolytic enzyme" (E.C. 3.1.1), what is meant herein is a lipase (E.C. 3.1.1.3) or a cutinase (E.C. 3.1.1.50) which is capable of removing stains of a fatty nature. Lipase has higher selectivity toward long chain triglycerides contained in fat than cutinase. Cutinase has higher selectivity toward short chain triglycerides contained in fat than lipase.

It is a primary object of the present invention to provide novel lipases which, when incorporated in a detergent composition, are capable of removing fatty acid based dirt and stains from fabrics.

It is another primary object of the present invention to provide a novel cutinase which, when incorporated in a detergent composition, is capable of removing fatty acid based dirt and stains from fabrics.

Still another primary object of the present invention is to provide novel enzyme compositions of lipases and/or cutinases which, when incorporated in a detergent composition, are capable of removing fatty acid based dirt and stains from fabrics.

A further primary object of the present invention is to identify, isolate and provide a biologically pure culture of a novel fungus of the genus Fusarium which is capable of naturally producing the lipolytic enzymes, including the lipases and cutinases, of the present invention which lipolytic enzymes may be incorporated into the enzymatic compositions and/or the detergent compositions of the present invention.

A yet further primary object of the present invention is to provide a method for removing fatty acid-based dirt and stains from fabrics with the use of the enzymes and/or the enzyme compositions of the present invention.

A still yet further object of the present invention is to provide an enzymatic detergent composition capable of removing fatty acid-based dirt and stains from fabrics, which detergent composition includes a lipolytic enzyme and/or a lipase and/or cutinase and/or enzyme composition.

In accordance with the teachings of the present invention, disclosed herein is a biologically pure culture of the novel isolate *Fusarium solanii* var. *minus* T.92.637/1 and mutants and derivatives thereof. This isolate is capable of producing the lipolytic enzymes, the lipases, the cutinases and the enzyme compositions of the present invention.

In another aspect of the present invention, disclosed herein are novel lipolytic enzymes which are naturally produced by an isolate of the species Fusarium and, more particularly, of the species *Fusarium solanii*. The preferred enzymes are those lipolytic enzymes which are naturally produced by the isolate *Fusarium solanii* var. *minus*. The most preferred enzymes are those lipolytic enzymes which are naturally produced by the isolate *Fusarium solanii* var. *minus* T.92.637/1.

In one preferred embodiment, the lipolytic enzymes of the present invention include a lipase having an isoelectric point of about 6.9 and/or an apparent molecular weight of about 30 kDa. In another preferred embodiment, the lipolytic enzymes include a lipase having an isoelectric point of about 5.2 and/or an apparent molecular weight of about 60 kDa. In still another preferred embodiment, the lipolytic enzymes include a cutinase having an isoelectric point of about 7.2 and/or an apparent molecular weight of about 22 kDa.

In a yet further aspect of the present invention, disclosed herein are novel enzyme compositions having at least one lipolytic enzyme which is naturally produced by a fungus of the species Fusarium and, more particularly, from the species *Fusarium solanii*. Most preferred are those enzyme compositions having at least one lipolytic enzyme which is naturally produced by the isolate *Fusarium solanii* var. *minus* T.92.637/1.

In a preferred embodiment, the lipolytic enzyme of the enzyme compositions is a lipase having an isoelectric point of about 6.9 and/or an apparent molecular weight of about 30 kDa. Alternatively, the lipolytic enzyme of the enzyme compositions is a lipase having an isoelectric point of about 5.2 and/or an apparent molecular weight of about 60 kDa. Still further alternatively, the lipolytic enzyme of the enzyme compositions is a cutinase having an isoelectric point of about 7.2 and/or an apparent molecular weight of about 22 kDa.

In a further preferred embodiment, the enzyme compositions contain at least two of the aforesaid lipolytic enzymes. In one preferred embodiment, the lipolytic enzymes are a lipase having an isoelectric point of about 6.9 and/or an apparent molecular weight of about 30 kDa and a lipase having an isoelectric point of about 5.2 and/or an apparent molecular weight of about 60 kDa. In an alternative preferred embodiment, the lipolytic enzymes are a lipase having an isoelectric point of about 6.9 and/or an apparent molecular weight of about 30 kDa and a cutinase having an isoelectric point of about 7.2 and/or an apparent molecular weight of about 22 kDa. In still another alternative preferred embodiment, the lipolytic enzymes are a lipase having an isoelectric point of about 5.2 and/or an apparent molecular weight of about 60 kDa and a cutinase having an isoelectric point of about 7.2 and/or an apparent molecular weight of about 22 kDa.

Most preferred are those enzyme compositions that contain all three of the lipolytic enzymes. Such compositions have a lipase having an isoelectric point of about 6.9 and/or an apparent molecular weight of about 30 kDa and a lipase having an isoelectric point of about 5.2 and/or an apparent molecular weight of about 60 kDa and a cutinase having an isoelectric point of about 7.2 and/or an apparent molecular weight of about 22 kDa.

In a still yet further aspect of the present invention, disclosed herein are novel enzymatic detergent compositions having at least one lipolytic enzyme which is naturally produced by a fungus of the species Fusarium and, more particularly, from the species *Fusarium solanii*. Most preferred are those enzymatic detergent compositions having at least one lipolytic enzyme which is naturally produced by the isolate *Fusarium solanii* var. *minus* T.92.637/1.

In a preferred embodiment, the lipolytic enzyme of the enzymatic detergent compositions is a lipase having an isoelectric point of about 6.9 and/or an apparent molecular weight of about 30 kDa. Alternatively, the lipolytic enzyme of the enzymatic detergent compositions is a lipase having an isoelectric point of about 5.2 and/or an apparent molecular weight of about 60 kDa. Still further alternatively, the lipolytic enzyme of the enzymatic detergent compositions is a cutinase having an isoelectric point of about 7.2 and/or an apparent molecular weight of about 22 kDa.

In a further preferred embodiment, the enzymatic detergent compositions contain at least two of the aforesaid lipolytic enzymes. In one preferred embodiment, the lipolytic enzymes are a lipase having an isoelectric point of about 6.9 and/or an apparent molecular weight of about 30 kDa and a lipase having an isoelectric point of about 5.2 and/or an apparent molecular weight of about 60 kDa. In an alternative preferred embodiment, the lipolytic enzymes are a lipase having an isoelectric point of about 6.9 and/or an apparent molecular weight of about 30 kDa and a cutinase a having an isoelectric point of about 7.2 and/or an apparent molecular weight of about 22 kDa. In still another alternative preferred embodiment, the lipolytic enzymes are a lipase having an isoelectric point of about 5.2 and/or an apparent molecular weight of about 60 kDa and a cutinase a having an isoelectric point of about 7.2 and/or an apparent molecular weight of about 22 kDa.

Most preferred are those enzymatic detergent compositions that contain all three of the lipolytic enzymes. Such compositions have a lipase having an isoelectric point of about 6.9 and/or an apparent molecular weight of about 30 kDa and a lipase having an isoelectric point of about 5.2 and/or an apparent molecular weight of about 60 kDa and a cutinase having an isoelectric point of about 7.2 and/or an apparent molecular weight of about 22 kDa.

The enzymatic detergent compositions of the present invention are all capable of removing fatty acid-based dirt and stains from fabrics.

These and further objects and advantages of the present invention will become readily apparent from a reading of the following description.

The novel isolate of the present invention is a biologically pure culture of the isolate *Fusarium solanii* var. *minus* T.92.637/1.

The fungus *Fusarium solanii* var. *minus* T.92.637/1 was deposited under the provisions of the Budapest Treaty on Nov. 23, 1993 with the BELGIAN COORDINATED COLLECTIONS OF MICROORGANISMS (MUCL: THE AGRICULTURAL AND INDUSTRIAL FILAMENTOUS AND YEAST FUNGI COLLECTION, Mycothéque de l'Université Catholique de Louvain, Place Croix du Sud 3, B-1348 Louvain-La-Neuve, Belgium under accession number MUCL 38667).

The morphological characteristics of *Fusarium solanii* var. *minus* T.92.637/1 are set forth in detail below in Example 1.

Natural and artificial mutants and derivatives of *Fusarium solanii* var. *minus* T.92.637/1 may be obtained by natural modifications or by genetic modifications thereof. Such well known methods as, for example, by X-ray techniques, ultraviolet irradiation, chemical mutagens or genetic engineering can all be employed to obtain such mutants and derivatives. It is to be expressly understood that such mutants and derivatives are also contemplated and encompassed by the present invention. The novel lipolytic enzymes, lipases, cutinases and enzyme compositions of the present invention are naturally produced by a fungus of the genus Fusarium and, more particularly, from the isolate *Fusarium solanii* var. minus T.92.637/1.

The lipolytic enzymes, lipases, cutinases and enzyme compositions of the present invention are naturally produced during the growth of the fungus and are substantially extracellularly excreted (secreted) into the medium. These lipolytic enzymes, lipases, cutinases and enzyme compositions may be recovered using normal techniques, generally comprising centrifugation to remove the fungal cells, followed by concentration by ultrafiltration. The crude lipolytic enzymes, lipases, cutinases and enzyme compositions obtained in this way can then be dried. An additional purification stage is also possible in order to separate contaminating proteins from the lipolytic enzymes, lipases, cutinases and enzyme compositions of the present invention. One of the lipases of the present invention is characterized by having an isoelectric point of about 5.2 and an apparent molecular weight of about 60 kDa. Another of the lipases of the present invention is characterized by having an isoelectric point of about 6.9 and an apparent molecular weight of about 30 kDa. The cutinase of the present invention is characterized by having an isoelectric point of about 7.2 and an apparent molecular weight of about 22 kD.

The enzyme compositions of the present invention are comprised of the lipolytic enzymes and/or lipases and/or cutinases of the present invention. More particularly, the enzyme compositions include either at least one lipase and/or at least one cutinase naturally produced by *Fusarium solanii* var. *minus.* T.92.637/1. In a preferred embodiment, the enzyme composition of the present invention includes at least one of the lipases and at least one of the cutinases naturally produced by *Fusarium solanii* var. *minus.* T.92.637/1. In another embodiment, the enzyme composition includes the lipases which are naturally produced by *Fusarium solanii* var. *minus.* T.92.637/1. Most preferred, is that enzyme composition includes the lipases and the cutinases naturally produced by *Fusarium solanii* var. *minus.* T.92.637/1.

The lipolytic enzymes (lipases and cutinases) and enzyme compositions of the present invention have use in a number of varying applications for hydrolyzing and modifying fats, ranging from, inter alia, oleochemistry processing applications to soap and detergent compositions. For example, the lipases of the present invention have utility for the interesterification of oils and fats, esterification of fatty acids, digestive aids in animal feeds and in flavor enhancement (as an additive in dairy products, such as milk) in the dairy industry.

The novel lipases, cutinases and enzyme compositions of the present invention are particularly useful for the removal of fatty acids from fabrics. In this regard, they may be used in combination with detergents in enzymatic detergent compositions and as an additive to washing and cleaning products. If desired, they may also be used in combination with one another and/or with other proteins, in particular enzymes including but not limited to amylases, alkaline proteases and oxidases.

Detergent compositions of the invention comprise one or more surfactants, at least one lipolytic enzyme of the invention, one or more other enzymes, detergent builders, bleaching system, detergent additives, enzymes stabilizers. Examples of surfactants are anionic, nonionic, cationic, or zwitterionic surfactants, usually anionic, such as linear alkylbenzenesulfonate; nonionic, such as alcohol ethoxylate. Other enzymes may include amylase, protease, cellulase, peroxidase or oxidase. Suitable detergent builders include zeolites, di- or triphosphates. Suitable detergent additives include carbohydrate binders, such as dextrins or cellulose derivatives, for instance hydroxypropyl cellulose, methyl cellulose. Suitable enzymes stabilizers include propylene glycol, sorbitol or other agents known as stabilizers for enzymes. The detergent compositions have a pH between 7 and 11 in aqueous solution at the use concentration.

The detergent composition can be either liquid or solid. It may contain the preparation as a granulate. It may be liquid and contains the preparation as an anhydrous or substantially anhydrous slurry.

Factors such as pH range, tolerance of emulsifiers and surfactants, temperature tolerance and storage capability are important considerations in the selection and development of commercially useful lipases and cutinases.

The present invention further concerns a method for removing fat stains from fabrics: this method comprises washing said fabrics with a detergent composition including a detergent active composition and an effective amount of the lipolytic enzyme and/or lipase and/or cutinase and/or enzyme composition of the present invention. In the washing process, the detergent composition used is the detergent according to the invention and in which the pH of the detergent composition is between 7 and 11 and the temperature is below 60 ° C. In a preferred embodiment of the invention, the washing solution contains the detergent composition according to the invention in an amount of between 1 and 5 g/l of washing solution.

Having thus described the *Fusarium solanii* var. *minus* T.92.637/1, methods for the cultivation of a biologically pure culture thereof, methods to produce and obtain the lipolytic enzymes, lipases, cutinases and enzyme compositions of the present invention therefrom, detergent compositions including such enzymes and/or enzyme compositions and methods for the use of the detergent compositions of the present invention having such lipases, cutinases and enzyme compositions for the removal of fatty acids from fabrics, the following examples are now presented for purposes of illustration only and are neither meant to be, nor should they be read as being, restrictive thereof.

EXAMPLE 1

Isolation and Selection of *Fusarium solanii* var. *minus* T.92.637/1

*Fusarium solanii* var. *minus* T.92.637/1 was isolated from a sample of soil on an agar nutrient medium.

The agar nutrient medium, called medium K, on which the isolates were isolated and selected was comprised of (per liter of distilled water) 5.0 grams of Bacto-Tryptone (DIFCO); 1.0 gram of $NaNO_3$; 1.0 gram of $MgSO_4 \cdot 7H_2O$; 1.0 gram of $K_2HPO_4$; 0.5 grams of KCl 10.0 grams of olive oil (in emulsion); 1.0 gram of polyvinylic alcohol (25/140) (in emulsion); 20 grams of agar; and 1.0 ml of 1% (w/v) Rhodamine solution (w=weight, v=volume).

The medium K was prepared as follows:

Firstly, an olive oil emulsion was prepared. 50 ml of the distilled water was heated to 80° C. Then, the 1.0 gram of the polyvinylic alcohol was added to the heated distilled water in small incremental steps. Next, 10 grams of olive oil was added to the distilled water/polyvinylic alcohol and the mixture emulsified by agitation for 5 minutes at 13500 RPM (revolutions per minute) in a blender (ULTRA TURRAX, mixing shaft 18 GM). An olive oil emulsion was obtained. The olive oil emulsion was then sterilized by autoclave at 121 ° C. for 30 minutes.

Secondly, an agar medium was prepared. The Bacto-Tryptone, $NaNO_3$, $MgSO_4 \cdot 7H_2O$, KCl and agar were added in 950 ml of the distilled water. The mixture was then sterilized by autoclave for 30 minutes at 121° C.

Thirdly, the Rhodamine solution was sterilized extemporaneously by filtration on 0.45 micron membranes.

Then, the olive oil emulsion and the agar were permitted to cool down to 60° C. before the emulsion was added to the agar. The 1 ml of Rhodamine was then added thereto. The mixture was then further mixed for five minutes in a blender (Ultra Turrax equipped with 25 F mixing shaft) at 13500 RPM. Then, and before solidification, the 25 ml of the medium K so obtained was placed in respective suitable sterile Petri dishes (9 cm in diameter) for subsequent use.

The samples to be screened were cultured at 25° C. for 48 hours on the medium K and appropriate isolates were selected for their ability to degrade olive oil and, in the presence of Rhodamine, produce a fluorescent halo under UV light.

The isolate of the present invention has been identified by its biochemical characteristics on the nutritive medium POTATO DEXTROSE AGAR (DIFCO).

Species of Fusarium are characterized by the shape of their conidia. *Fusarium solanii* is, above all, characterized by its formation of microconidia (phialoconidia) from very long slender conodiogenesis cell (phialide). Furthermore, those microconidia are agglomerated at the top of the conidiogenesis cell in a mucilaginous drop. Macroconidia are also typical as well as the formation of smooth to rough chlamydospore.

The distinction between *Fusarium solanii* var. *minus* and other varieties of that species is based on the state of the macroconidia which are smaller in the variety minus than in other varieties.

The characteristics of the strain *Fusarium solanii* var. *minus* T.92.637/1 are as follows:

colonies are fast growing, up to 80 mm in 10 days.
aerial mycelium white to cream delicate.
microconidia develop abundantly yet after some days of growing.
microconidia are more or less oval to ellipsoid, thin to slightly thick walled, 8 to 13 $\mu$m×2.5 to 3.5 $\mu$m unicellular to bicellular.
microconidia are produced from very long slender phialide (monophialidic) with a rather distinct collar, solitary or verticillate, up to 100 $\mu$m long.
macroconidia 1 to 3 septate, subcylindric or slightly curved, up to 30 $\mu$m long, produced from shorter phialide, up to 20 $\mu$m.
chlamydospores more or less abundant, terminal or intercalary, smooth to rough-walled, single or in pairs, globose to subglobose, 5.5 $\mu$m×8 $\mu$m.

*Fusarium solanii* var. *minus* isolate T.92.637/1 was deposited under the provisions of the Treaty of Budapest on Nov. 23, 1993 in the Belgian Coordinated Collections of Microorganisms (BCCM culture collection, MUCL) under Accession Number MUCL 38667.

EXAMPLE 2

Obtaining Pure Culture of *Fusarium solanii* var. *minus* isolate T.92.637/1

First, a Potato Dextrose Agar (PDA) culture medium was prepared using 39 grams/liter of Bacto Potato Dextrose Agar (DIFCO) supplemented with 12 mg of tetracycline per liter of agar culture medium.

10 ml of the medium was poured into respective 160/16 tubes and the tubes were then inclined and left to solidify. After solidification, the various tubes were inoculated with the selected isolates which were obtained and identified as described in example 1. The culture was then developed after an incubation of 48 to 72 hours at 25° C. The tubes were then stored at approximately 4° C. until use thereof.

The cultures obtained as described above were then identified as being pure cultures of *Fusarium solanii* var. *minus* isolate T.92.637/1. This identification was confirmed by the use of common taxonomic tests.

EXAMPLE 3

Production of Enzymes Derived From *Fusarium solanii* var. *minus* T.92.637/1

A medium was prepared comprised of (per liter of distilled water) 5 grams of Bacto-Tryptone (DIFCO); 1.0 gram of $NaNO_3$; 1.0 gram of $MgSO_4,7H_2O$; 1.0 gram of $K_2HPO_4$; 0.5 grams of KCl; 10.0 grams of soya oil; and 5.0 grams of Mazuöl (Mazes Chemicals).

The medium was prepared by mixing together all of the components mentioned above, with the exception of the soya oil, and then adjusting the pH to 6.5 with 0.1 N HCl. This mixture was then sterilized by autoclave at 121° C. for 30 minutes.

The soya oil component of the medium was prepared extemporaneously by the sterilization thereof by autoclave for 30 minutes at 121° C.

After sterilization, the soya oil emulsion and the nutrient medium were permitted to cool down to 60° C. before being mixed together. The resulting medium was designated CH2 medium.

A physiological saline serum of distilled water and 0.9% (w/v) NaCl was prepared and sterilized by autoclaving (at about 1.4–1.5 bars) at 121° C. for 30 minutes. 10 ml of this physiological serum was added to respective inclined tubes (slants) containing the pure Fusarium culture obtained as described in Example 2. These tubes were then lightly manually agitated to place the Fusarium in the respective inclined tubes in suspension. These tubes constituted the inoculum which were then used for subsequent inoculations.

Respective 50 ml samples of CH2 medium were then placed in respective sterile 500 ml Erlenmeyer flasks. 0.5 ml of physiological serum containing the Fusarium suspension were then introduced into each tube and incubated at 25° C. for 24 hours under agitation (orbital movement of 65 revolutions per minute with approximately 2.54 cm amplitude).

Control of the purity of the conidia was done by microscopic observation to assure noncontamination of the suspension of conidia.

Incubation of culture flasks, as described above, resulted in, inter alia, the extracellular production of both lipases and cutinases. These *Fusarium solanii* var. *minus* T.92.637/1 lipases and cutinases are secreted into the culture broth in the culture flask.

The presence of the lipases and cutinases which are naturally produced by *Fusarium solanii* var. *minus* T.92.637/1 in the culture broth was then confirmed, as is described below in Example 4.

EXAMPLE 4

Titrimetric Lipases and Cutinases Activity Test

An Erlenmeyer flask of Example 3 containing a Fusarium culture was obtained and the culture broth thereof was tested for lipase activity and cutinase activity.

Determination of the lipase and cutinase activity in the culture broth was performed as follows:

A substrate emulsion was prepared comprised of: 10 grams of Triolein (ROTH 5423); 10 grams of *Gummi arabicum* (Fluka No. 51 200) and 100 ml of deionized water. This mixture was emulsified for 15 minutes in a blender (Ultra Turrax equipped with 25 F mixing shaft at 13500 rpm) in ice while being steadily stirred in a pure nitrogen gas atmosphere.

A buffer was prepared comprised of TRIS 5mM, NaCl 40 mM and 20 mM of $CaCl_2,2H_2O$.

The culture broth of the samples obtained as described above in Example 3 were then used to prepare active samples and inactive (for providing a standard) samples therefrom. Active samples were prepared by diluting the culture broth obtained from the samples of Example 3 by mixing approximately 1 part broth with approximately 50 parts (v/v) of the buffer (so that an enzyme concentration of approximately 2 LU/ml is provided). Inactive samples were prepared in the same manner as the active samples except that after the dilution, the inactive samples were inactivated by being heated at 110° C. for 30 minutes.

First, a reaction vessel (a cylindrical reaction vessel having a dimension of 24 mm×100 mm and equipped with a pH electrode—Schott No. 6880) was filled with 10 ml of the substrate emulsion and 20 ml of the buffer. Nitrogen gas was then pumped into the vessel to provide a pure nitrogen gas atmosphere in the vessel and the mixture stirred. The temperature of the vessel was then raised to 30° C.

Next, the pH of the solution was adjusted to 9.5 using 0.5N NaOH. Then, 0.25 to 0.5 ml of the sample to be tested was added to the reaction vessel and monitoring of the titrations started. The pH of the solution was maintained at 9.5 with the addition of 0.01N NaOH, as needed. Titrations were then carried out at 30° C. using 0.01N NaOH as the alkali.

After two minutes, the total amount of added 0.01N NaOH was monitored for the next two minutes (until the titration was completed).

As used herein, LU stands for Lipase and Cutinase Units. As used herein, one lipase and cutinase unit is the amount of lipase/cutinase which is necessary to liberate one $\mu$mol fatty acid per minute by 1 ml of the sample being tested under the conditions of the test.

The above Titration demonstrated that the culture broth of the Fusarium isolate of the present invention had a lipase activity and a cutinase activity, as well as properties of long chain hydrolysis of lipids.

EXAMPLE 5

Fatty Acids Selectivity of Lipase and Cutinase

Two media were prepared to identify lipase activity and cutinase activity.

A first medium, called medium T, was comprised of: (per liter of distilled water) 2.5 grams of $NaHCO_3$; 7.5 grams of $Na_2CO_3$; 10.0 grams of olive oil (in emulsion); 1.0 gram of polyvinylic alcohol (25/140) (in emulsion); 20 grams of agar; and 1.0 ml of 1% (w/v) Rhodamine solution.

A second medium, called medium V, was comprised of: (per liter of distilled water): 2.5 grams of $NaHCO_3$; 7.5 grams of $Na_2CO_3$; 10.0 grams of tributyrin (in emulsion); 1.0 gram of polyvinylic alcohol (25/140) (in emulsion); 20 grams of agar.

Medium V and medium T were both prepared in the same manner following the protocol of and under the conditions specified in the method of preparation of the medium K, as described in example 1. Respective Petri dishes having medium V or medium T were then prepared.

In each of the Petri dishes of medium V and of medium T so obtained, four separated holes were made.

5 microliters of the enzyme fraction to identify were deposited in the the four holes of a Petri dish containing the medium T and also in the four holes of a Petri dish containing the medium V.

The Petri dishes so obtained were incubated at 30° C. for 6 hours.

Large fluorescent zones appeared on the medium T of the Petri dishes around the holes, indicating a predominance of a lipase activity. This is due to the fact that a lipase has a higher selectivity toward long chain triglycerides than a cutinase.

Large clear zones appeared on the medium V of the Petri dishes around the holes, indicating a predominance of a cutinase activity. It is due to the fact that a cutinase has a higher selectivity toward short chain triglycerides than a lipase.

EXAMPLE 6

Preparation of Concentrated Lipases Solution from *Fusarium solanii* var. *minus* T92.637/1

The culture flasks, obtained as described above in Example 3, were used as the inoculum for a fermentation.

13 liters of fermentation medium was prepared comprised of (per liter of distilled water) 30 grams of tryptone (Merck 7214); 50 grams of soya oil; 5 grams of methylcellulose (Culminal 1500 PFR); 1 gram of Mazuol (Mazes Chemicals): 1 gram of $NaNO_3$; 1 gram of $MgSO_4,7H_2O$; 2 grams of $K_2HPO_4$; 0.5 grams of KCl. The pH of the medium was adjusted to 6.5 with HCl 0.1N. The medium was sterilized at 121° C. for 30 minutes.

A fermentation was then conducted at 25° C. for 82 hours under constant stirring of 450 RPM (rotation per minute) and aeration of 0.3 VVM (volume per volume per minute).

A sample of the resulting fermenter beer was tested as described above in Example 4, in order to determine lipase/cutinase activity. Following a finding of lipase/cutinase activity, the resulting fermenter beer was concentrated as follows.

First, the pH of the fermenter beer was adjusted to 8.5 with NaOH 10N. Then, 2.0% (w/v) of OPTIFLOC FC 205 (SOLVAY) was added together with 1.0% (w/v) of Triton X-114 (Serva) and mixed therewith for one hour with gentle agitation. This mixture was then centrifuged at 8000 RPM (Beckman, rotor JA-10) for 15 minutes at 4° C. The supernatant was then fractionated by ammonium sulphate precipitation (saturation range: 20–60%). A fractioned precipitate was recovered.

The fractioned precipitate was dissolved in 100 ml of an appropriate buffer (BRIJ58 5mM (ICI); $CaCl_2$ 25 mM; Tris/HCl 20 mM, pH 7.0). A concentrated lipases solution was thus obtained.

EXAMPLE 7

Purification of the Lipases

A concentrated lipases solution was obtained, as described above in Example 6. First, the lipases of this solution were isolated (extracted) from the solution by hydrophobic interaction chromatography (HIC). The extracted (isolated) lipases were then purified by ionic exchange chromatography (IEC) and gel filtration.

The column used for the hydrophobic interaction chromatography (HIC) is a column of Hiload 16/10 Phenyl Sepharose High Performance (PHARMACIA 17-1085-01) with the following characteristics for the first run.

40 ml of the concentrated lipases solution as obtained in Example 6 is diluted by the starting buffer, so as to obtain 250 ml of solution to be loaded on the HIC column.

The buffers used for the HIC were the following
Starting buffer: potassium phosphate 20 mM pH 7.0
Elution buffer: potassium phosphate 20 mM pH 7.0+ isopropanol 30% (v/v).

The flow rate was adjusted to 1.5 ml/min. The gradient was 0–100%.

89.3% of the lipases were eluted in the isopropanol gradient in a 60 ml fraction.

For the second run, the 60 ml lipases fraction was then diluted with 120 ml of the starting buffer and then the 180 ml diluted solution was reloaded on the same column in the same conditions.

59.4% of the lipase was eluted in the isopropanol gradient in a 45 ml fraction.

The 45 ml fraction was then diafiltrated on an AMICON cell (76 mm cell), equipped with a YM10 membrane, against 10 parts (v/w) of the starting buffer of the IEC chromatography.

Purification of the lipases from the fraction was then performed by ionic exchange chromatography (IEC) with the following characteristics.

The column used for the ionic exchange chromatography (IEC) is a column of Hiload 16/10 Q-Sepharose High Performance (PHARMACIA 17-1064-01) with the following characteristics.

The 45 ml diafiltrated solution was diluted with 195 ml of the starting buffer of the IEC chromatography.

The buffers used for the IEC were the following
Starting buffer: Piperazine 20 mM pH 9.7
Elution buffer: Piperazine 20 mM pH 9.7+NaCl 1.0 M (0–100% gradient).

The flowrate was adjusted to 3.0 ml/min.

100% of the lipases were eluted within the NaCl gradient in a 27 ml fraction.

Fractions were then concentrated on AMICON cell (76 mm cell equipped with a YM10 membrane) and diafiltrated against 10 parts (v/w) of Tris/HCl 20 mM (pH 7.0) comprising a $CaCl_2$ 5 mM buffer.

A gel filtration, with the following characteristics, was then used:

The column used was a column of Superdex 75 HR 10/30 (PHARMACIA 17-1047-01) using a buffer of CAPSO [3-(cyclohexylamino)-2-hydroxy-1-propane sulfonic acid] 25 mM (pH 9.2) with 0.2 M NaCl.

The flowrate was adjusted to 0.5 ml/min. Fractions were obtained, each of which corresponded to a separate peak, thus showing that two different lipases were obtained.

Lipase identification was made according to the method described above in Example 5. This identification revealed the presence of two separate lipases in the fraction.

The ratio of the diameters of the clear zone and the fluorescent zone was been determined for each fraction. For each fraction, the ratio was in the range of about 0.05 and 0.1. This result confirmed the presence of lipase activity.

EXAMPLE 8

Preparation of Concentrated Cutinases Solution from *Fusarium solanii* var. *minus* isolate T.92.637/ 1

A medium was prepared comprised of (per liter of distilled water): 5 grams of Bacto-Tryptone (DIFCO); 1.0 gram of $NaNO_3$; 1.0 gram of $MgSO_4,7H_2O$; 1.0 gram of $K_2HPO_4$; 0.5 grams of KCl; 5.0 grams of purified cutin; and 5.0 grams of Mazuöl (Mazes Chemicals).

Purified Cutin was obtained from Golden Delicious Apple according to the method described by Hervé C. Gérard, in Phytochemical Analysis, Vol.3, 139–144 (1992).

The medium was prepared by mixing together all of the components mentioned above and then adjusting the pH to 6.5 with 0.1 N HCl. This mixture was then sterilized by autoclave at 121° C. for 30 minutes.

After sterilization, the nutrient medium was permitted to cool down to 60° C., then to 25° C. before ionculation.

A physiological saline serum of distilled water and 0.9% (w/v) NaCl was prepared and sterilized by autoclaving (at about 1.4–1.5 bars) at 121° C. for 30 minutes. 10 ml of this physiological serum was added to respective inclined tubes (slants) containing the pure Fusarium culture obtained as described in Example 2. These tubes were then lightly manually agitated to place the Fusarium in the respective inclined tubes in suspension. These tubes constituted the inoculum which were then used for subsequent inoculations.

Respective 50 ml samples of the culture medium were then placed in respective sterile 500 ml Erlenmeyer flasks. 0.5 ml of physiological serum containing the Fusarium suspension were then introduced into each tube and incubated at 25° C. for 24 hours under agitation (orbital movement of 65 revolutions per minute with approximately 2.54 cm amplitude).

Control of the purity of the conidia was done by microscopic observation to assure noncontamination of the suspension of conidia.

The culture flask, obtained as described above, was used as the inoculum for a fermentation.

1 liter of fermentation media was prepared comprised of the medium described above.

A fermentation was then conducted at 25° C. for 64 hours under constant stirring of 1000 RPM and aeration of 0.3 VVM.

A sample of the resulting fermenter beer was tested as described above in Example 4, in order to determine lipase/cutinase activity. Following a finding of lipase/cutinase activity, the resulting fermenter beer was then treated as follows.

The fermenter beer was centrifuged at 8000 rpm (SW 27 rotor) for 15 minutes. The biomass was then diluted by addition of the same amount of demineralised water as the removed supernatant and then treated for 1 hour with 1% w/w of Triton X-114 (SERVA reference 37243). The diluted, treated biomass was then once again centrifuged at 8000 rpm (SW 27 rotor) for 15 minutes.

The supernatant was fractionated by aceton (saturation range 35–60%). A precipitate was recovered. The precipitate was then dissolved in 100 ml of an appropriate buffer (Tris/HCl 20 mM pH 7, $CaCl_2$ 5 mM). A concentrated lipases/cutinases solution was so obtained.

EXAMPLE 9

Separation of the Lipase and the Cutinase and Purification of the Same

A concentrated cutinases solution was obtained in the manner described above in Example 8. The cutinases were then purified from the concentrated cutinases solution by Hydrophobic Interaction Chromatography (HIC).

The column used is a column of Hiload 16/10 Phenyl Sepharose High Performance. (PHARMACIA 17-1085-01).

The chromatography was performed having the following characteristics.

15 ml of the concentrated lipases solution, obtained as described above in Example 8, was diluted by the starting buffer, so as to obtain 250 ml of a solution to be loaded on the HIC column.

The buffers used for the HIC were potassium phosphate 20 mM pH 7.0 for the starting buffer and potassium phosphate 20 mM pH 7.0+isopropanol 30% (v/v) (0–100% gradient) for the elution buffer. The flowrate is adjusted to 1.5 ml/min.

54.6% of the lipolytic enzymes(s) were not adsorbed on the column (240 ml active non-adsorbed fraction) while 17.2% of the lipolytic enzymes were eluted into the isopropanol gradient (27 ml active adsorbed fraction).

Cutinase and lipase identifications were made according to the method described above in example 5.

A cutinase was identified to be present in the active non-adsorbed fraction and a lipase was identified to be present in the active adsorbed fraction.

The ratio of the diameters of the clear zone and the fluorescent zone was then determined for each fraction. For the active non-adsorbed fraction, the ratio was in the range of about 10 and 20. This result confirmed the presence of cutinase activity. For the active adsorbed fraction, the ratio was in the range of about 0.05 and 0.1. This result confirmed the presence of lipase activity.

EXAMPLE 10

Molecular Weight Determination by SDS-PAGE Analysis

Purified fractions of the lipases and the cutinases of the present invention were obtained as described above in, respectively, Examples 7 and 9. These fractions were then used in an SDS-PAGE analysis for an estimation of the molecular weights thereof.

The estimation of the molecular weights of the purified enzyme samples of the present invention by the use of SDS-PAGE analysis was effectuated in denaturing conditions on polyacrylamide gel using PHARMACIA PHAST-GEL 10–15% (w/v) by following the method described in separate technique file n° 110 PHASTSYSTEM. PHARMACIA LMW markers (cat n° 17-0446-01) were used for establishing the relation of molecular weight to migration distance. The following Pharmacia LMW markers were used as molecular weight standards: phosphorylase b (canine muscle) 94 kDa; albumin (bovine serum) 67 kDa; ovalbumin (chicken egg white) 43 kDa; carboanhydrase (bovine erythrocytes) 30 kDa; trypsin inhibitor (soy bean) 20.1 kDa; and alpha-lactalbumin (cow milk) 14.4 kDa.

One vial, diluted in 1.5 ml of the following buffer, was also used for the samples: 10 mM TRIS (pH of 8.0); 1 M EDTA; 2.5% (w/v) SDS (sodium dodecyl sulfate); 5% (v/v) beta-mercaptoethanol and 0.01% (w/v) bromophenol blue.

Each of the samples was first precipitated with trichloroacetic acid (final concentration 10% w/v), and was then diluted to a concentrated of approximately 100 μg protein/ml, measured by the method described by Lowry, 1951, J. Biol. Chem., 193, pages 256–275, in the same buffer as was described above for use in diluting the markers. The diluted samples were then denatured by heating at 98° C. for 15 minutes and 4 μl of the diluted, denatured samples were deposited on the gels. The gels were run for 60 Vh with a maximum voltage of 250 volts, a maximum power of 3 watts and maximum intensity of 10 mA.

After separation of the polypeptides, the gels were stained with Fast Coomassie as described in the Development Technique File No. 200 PHASTSYSTEM™.

The results of the SDS-PAGE analysis revealed four bands of about 30, 30, 22 and 60 kilodaltons (kDa).

The apparent molecular weight was found to be approximately:

30 kD for each of the two lipases fractions coming from Example 8,
22 kD for the active non-adsorbed fraction containing the cutinase coming from Example 9, and
60 kD for the active adsorbed fraction containing the lipase coming from Example 9.

EXAMPLE 11

Determination of the Isoelectric Point (pI) by Isoelectric Focusing

Purified solutions of the lipases and cutinase of the present invention were obtained as described above in Examples 7 and 9. These samples were then used for determination of the isoelectric point of the lipases and cutinases of the present invention by isoelectric focusing.

Isoelectric focusing was performed using PHARMACIA PHASTSYSTEM following the Separation Technique File No. 100 (PHASTSYSTEM™).

For this specific application, PHASTGEL IEF 3-9 was used. Pharmacia IEF markers were used (cat n° 17-0471-01).

The gels were stained with Fast Coomassie (Development Technique File N° 200 PHASTSYSTEM™).

The isoelectric points were found to be
6.9 for the two lipases fractions coming from Example 8,
7.2 for the active non-adsorbed fraction containing the cutinase coming from Example 9, and
5.2 for the active adsorbed fraction containing the lipase coming from Example 9.

Obviously many modifications may be made without departing from the basic spirit of the invention. Accordingly, it will be appreciated by those skilled in the art that within the scope of the appended claims, the invention may be practised other than has been specifically described herein.

We claim:

1. An isolated lipase naturally produced by a fungus of the species *Fusarium solanii* characterized in that the lipase has an isoelectric point of about 6.9 and an apparent molecular weight of about 30 kDa as determined by SDS-PAGE.

2. The lipase of claim 1 wherein the lipase is naturally produced by *Fusarium solanii* var. *minus*.

3. The lipase of claim 1 wherein the lipase is naturally produced by *Fusarium solanii* var. *minus* T.92637/1.

4. A detergent composition comprising the lipase of claim 1.

5. The detergent composition of claim 4 further comprising a second lipase characterized as having an isoelectric point of about 5.2 and an apparent molecular weight of about 60 kDa.

6. The detergent composition of claim 4 further comprising a cutinase.

7. The detergent composition of claim 6 wherein the cutinase is characterized as having an isoelectric point of about 7.2 and an apparent molecular weight of about 22 kDa.

8. A method for removing fat stains from fabrics, said method comprising washing said fabrics with a detergent composition of claim 4.

9. An enzyme composition comprising the lipase of claim 1.

10. The enzyme composition of claim 9 further comprising a second lipase naturally produced by a fungus of the species *Fusarium solanii*.

11. The enzyme composition of claim 10 wherein the second lipase is characterized as having an isoelectric point of about 5.2 and an apparent molecular weight of about 60 kDa.

12. The detergent composition of claim 14 further comprising a second lipase naturally produced by a fungus of the species *Fusarium solanii*.

13. The enzyme composition of claim 9 further comprising a cutinase.

14. The enzyme composition of claim 13 wherein the cutinase is characterized as having an isoelectric point of about 7.2 and an apparent molecular weight of about 22 kDa.

15. The detergent composition of claim 5 further comprising a cutinase.

16. The enzyme composition of claim 10 further comprising a cutinase.

17. The enzyme composition of claim 16 wherein the cutinase is characterized as having an isoelectric point of about 7.2 and an apparent molecular weight of about 22 kDa.

18. A method for removing fat stains from fabrics, said method comprising washing said fabrics with a detergent composition of claim 6.

* * * * *